(12) United States Patent
Imre

(10) Patent No.: US 7,733,486 B2
(45) Date of Patent: Jun. 8, 2010

(54) ENVIRONMENTAL SENSOR INCLUDING A BAFFLE

(75) Inventor: Kevin John Imre, Colton, CA (US)

(73) Assignee: Venturedyne, Ltd., Pewaukee, WI (US)

( * ) Notice: Subject to any disclaimer, the term of this patent is extended or adjusted under 35 U.S.C. 154(b) by 391 days.

(21) Appl. No.: 11/769,047

(22) Filed: Jun. 27, 2007

(65) Prior Publication Data
US 2009/0004447 A1     Jan. 1, 2009

(51) Int. Cl.
*G01N 21/00* (2006.01)

(52) U.S. Cl. ........................ 356/337; 356/338

(58) Field of Classification Search ......... 356/335–343, 356/44, 38–42, 237.1–237.3, 243.2, 243.4; 428/212; 239/290, 296, 299, 417.3, 424, 239/226, 106, 602
See application file for complete search history.

(56) References Cited

U.S. PATENT DOCUMENTS

| | | | |
|---|---|---|---|
| 3,312,826 A | 4/1967 | Finkle | |
| 3,409,885 A | 11/1968 | Hall | |
| 3,708,675 A | 1/1973 | Tashiro et al. | |
| 3,799,670 A | 3/1974 | Kohr | |
| 4,121,110 A | 10/1978 | Solomon | |
| 4,181,439 A | 1/1980 | Tresch et al. | |
| 4,206,366 A | 6/1980 | Marsocci et al. | |
| 4,216,377 A * | 8/1980 | Hasegawa et al. | 250/574 |
| 4,300,133 A | 11/1981 | Solomon | |
| 4,596,465 A | 6/1986 | Nagashima | |
| 4,728,801 A | 3/1988 | O'Connor | |
| 5,231,378 A | 7/1993 | Dennis et al. | |
| 5,515,164 A | 5/1996 | Kreikebaum et al. | |
| 5,600,438 A | 2/1997 | Kreikebaum et al. | |
| 5,799,875 A * | 9/1998 | Weinstein et al. | 239/296 |
| RE37,353 E | 9/2001 | Kreikebaum et al. | |
| 6,831,289 B1 | 12/2004 | Preikszas et al. | |

* cited by examiner

Primary Examiner—Gregory J Toatley, Jr.
Assistant Examiner—Tri T Ton
(74) Attorney, Agent, or Firm—Michael Best & Friedrich LLP

(57) ABSTRACT

A baffle for use with an environmental sensor such as a particle counter. The environmental sensor includes a housing and an inlet. The inlet has an axis and defines a first cross-sectional area with respect to the axis. The baffle includes a bullet configured to be positioned adjacent to the inlet along the axis. The bullet has a second cross-sectional area with respect to the axis that is between about seventy-five percent smaller than the first cross-sectional area and about three-hundred percent larger than the first cross-sectional area. In some constructions, the baffle substantially reduces interference from external light sources without substantially inhibiting the transport of particles entrained in the fluid to be analyzed by the environmental sensor.

31 Claims, 5 Drawing Sheets

ENVIRONMENTAL SENSOR INCLUDING A BAFFLE

BACKGROUND

The invention relates to an environmental sensor. More particularly, the invention relates to an environmental sensor having a baffle, which acts as a light blocker.

Environmental sensors are useful in a variety of applications. For example, environmental sensors include tobacco smoke monitors used to determine the dust content and tobacco content in the environment, digital dust indicators that use scattered light to determine the relative dust concentration in the environment, or digital dust monitors that use laser light to determine the relative dust concentration in the environment. Environmental sensors also include personal dust sensors used to measure and log personal exposure to aerosols, indoor pollution evaluating systems used to monitor, among other things, carbon dioxide and dust, and particle mass monitors used to quantify mass and size of airborne particles. Generally, the environmental sensors receive a fluid flow from the surrounding environment to monitor a property of the environment (e.g., a specific particle in the air). However, some environmental sensors may be susceptible to false or improper readings due to light from the environment.

In one application, the environmental sensor may be an airborne particle counter that draws an airflow though an inlet or air passage and into a scattering chamber to count and monitor particles (e.g., dirt, dust, microorganisms, etc.) in the airflow. The particle counter can illuminate the airflow with a light, causing particles within the airflow to scatter some of the light. The scattered light is reflected by mirrored surfaces in the scattering chamber onto a light sensitive detector, producing electrical pulses that are sized and counted.

SUMMARY

In some instances, ambient light (e.g., room light) may also enter the scattering chamber, striking various surfaces that form the air passage. This light may reflect and partially absorb at each surface it encounters. However, some room light enters the inlet substantially straight on (e.g., from a directly overhead light) and reflects only once or twice before striking the detector with considerable intensity. Ordinarily, this is not an issue since the illumination is constant. However, if the overhead illumination is from a high frequency flickering light source (e.g., a fluorescent light bulb powered by an electronic ballast), the resulting signals at the detector may resemble those of the scattered light from the particles. Electronic filtering of this high frequency light may be ineffective because the switching frequency of the electronic ballast that modulates the light may overlap the frequency bandwidth of electrical pulses produced by the scattered light from the particles. As such, a different solution is desired.

In one embodiment, the invention provides a baffle for use with a particle counter including a housing and an inlet. The inlet has an axis and defines a first cross-sectional area with respect to the axis. The baffle includes a bullet configured to be positioned adjacent to the inlet along the axis. The bullet has a second cross-sectional area with respect to the axis that is between about seventy-five percent smaller than the first cross-sectional area and about three-hundred percent larger than the first cross-sectional area.

In another embodiment, the invention provides a particle counter including a housing, an inlet having an axis, and a first cross-sectional area with respect to the axis, and a baffle. The baffle includes a bullet positioned adjacent to the inlet. The bullet has a second cross-sectional area with respect to the axis that is between about seventy-five percent smaller than the first cross-sectional area and about three-hundred percent larger than the first cross-sectional area.

In yet another embodiment, the invention provides an environmental sensor including a housing, an inlet having an axis, and a first cross-sectional area with respect to the axis, and a baffle. The baffle includes a bullet positioned adjacent to the inlet. The bullet has a second cross-sectional area with respect to the axis that is between about seventy-five percent smaller than the first cross-sectional area and about three-hundred percent larger than the first cross-sectional area.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
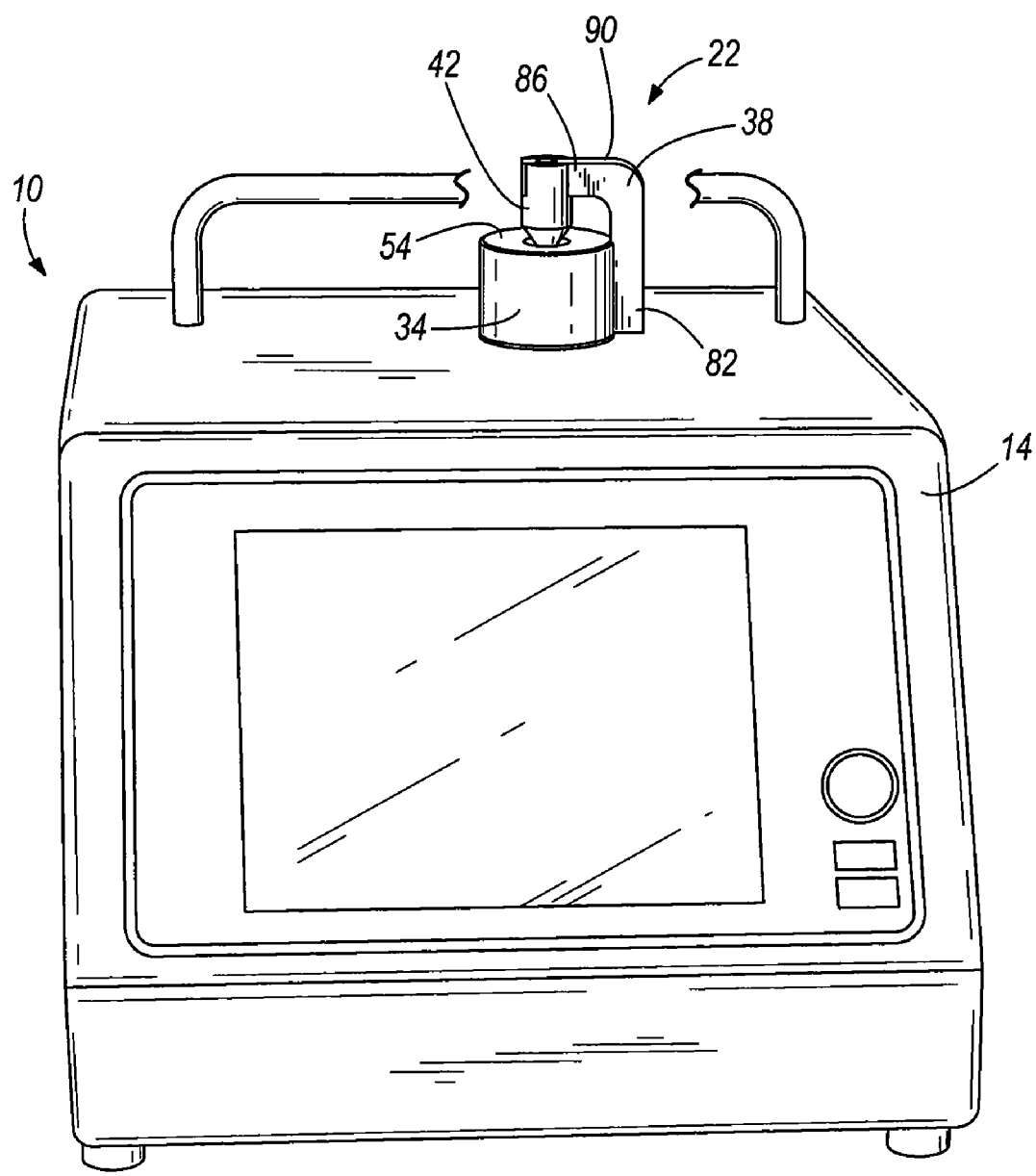
FIG. 1 is a perspective view of an environmental sensor, and more particularly a particle counter, including a baffle.
Figure 2:
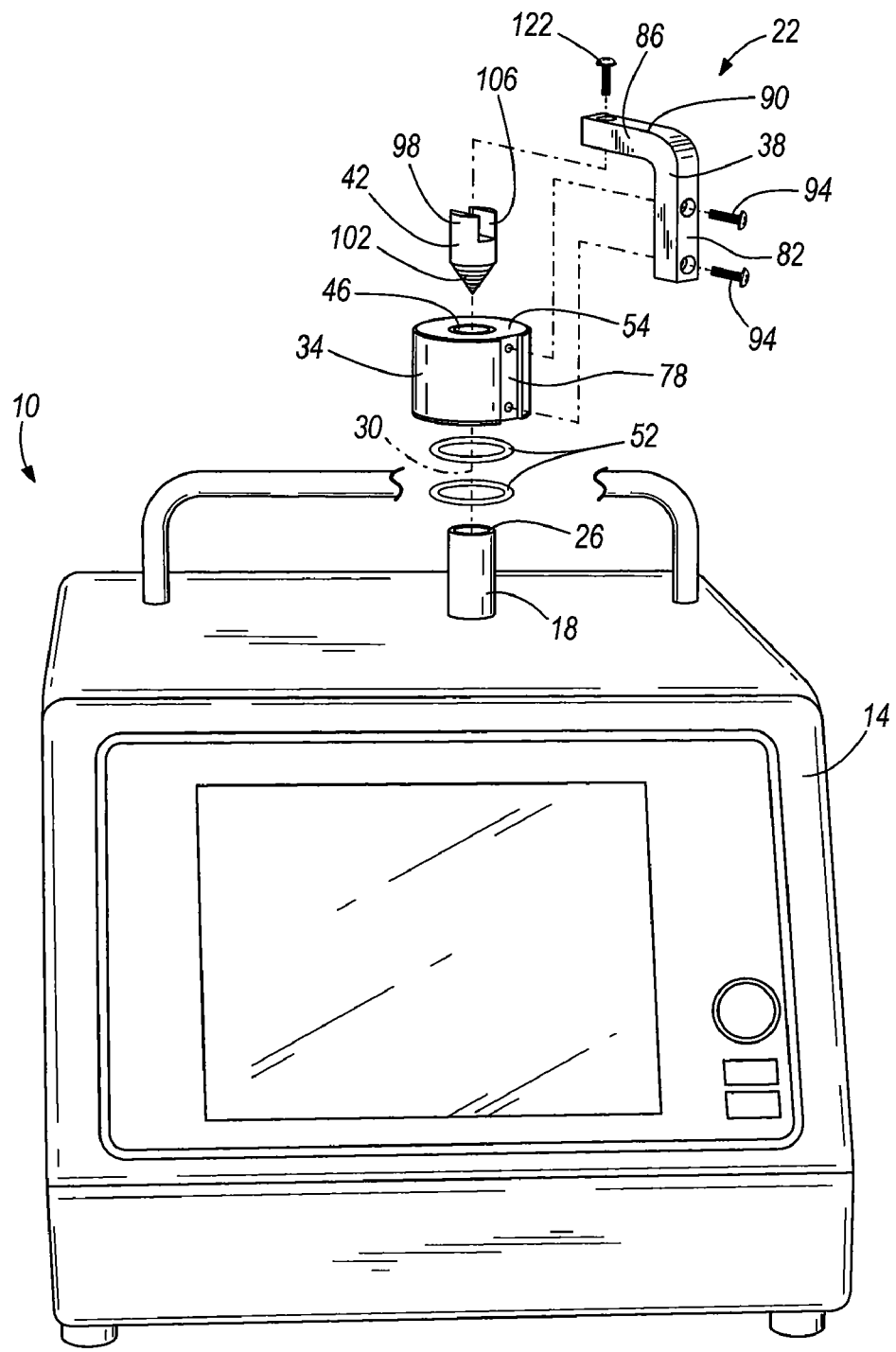
FIG. 2 is an exploded perspective view of the baffle on the environmental sensor shown in FIG. 1.

FIGS. 1 and 2 illustrate an environmental sensor used to monitor the surrounding environment. The environmental sensor draws an airflow from the surrounding environment and counts the number of particles in the airflow to determine the cleanliness of the environment. In the illustrated embodiment, the environmental sensor is a particle counter 10 used to count airborne particles (e.g., dust, dirt, microorganisms, etc.) in, for example, a pharmaceutical or semiconductor clean room. However, it should be readily apparent that the environmental sensor may alternatively be a tobacco smoke monitor, a digital dust indicator, a digital dust monitor, a personal dust sensor, an indoor pollution evaluating system, a particle mass monitor, or the like.

The illustrated particle counter 10 includes a housing 14, an inlet tube 18 coupled to the housing 14, and a baffle 22 coupled to the inlet tube 18. Likewise, alternative environmental sensors may include similar components arranged in a similar manner to the particle counter 10. It should also be understood that other environmental sensors may include additional components not normally associated with the particle counter 10.

The inlet tube 18 extends from the housing 14 and defines an inlet 26 having an axis 30 extending therethrough. In the illustrated construction, the inlet tube 18 is shown as a hollow cylinder having a generally circular cross-section. However, it should be readily apparent that the inlet tube 18 may have a different, non-circular cross-section such as, for example, a square, a hexagon, an oblong configuration, or the like. Additionally or alternatively, in some constructions, the inlet tube 18 may be omitted and the baffle 22 may be positioned directly adjacent to an aperture of the housing 14 that defines the inlet 26.

The baffle 22 is positioned adjacent to the inlet tube 18 to inhibit or restrict light from entering the housing 14 of the particle counter 10 without materially inhibiting airborne particles from entering. For example, the baffle 22 can substantially inhibit ambient light from entering the inlet tube 18 while still allowing five micron or larger particles to flow through the inlet tube 18 uninterrupted. When used with any of the alternative environmental sensors, the baffle 22 functions in a substantially similar manner to limit light entry, but maintain approximately the same amount of fluid flow into the environmental sensor. In the illustrated construction, all or a portion of the baffle 22 is composed of aluminum, and surfaces of the baffle 22 are hard black anodized to control and minimize light reflections. In other constructions, the baffle 22 may be composed of other suitable materials and/or different surface treatments may be used.

Figure 3:
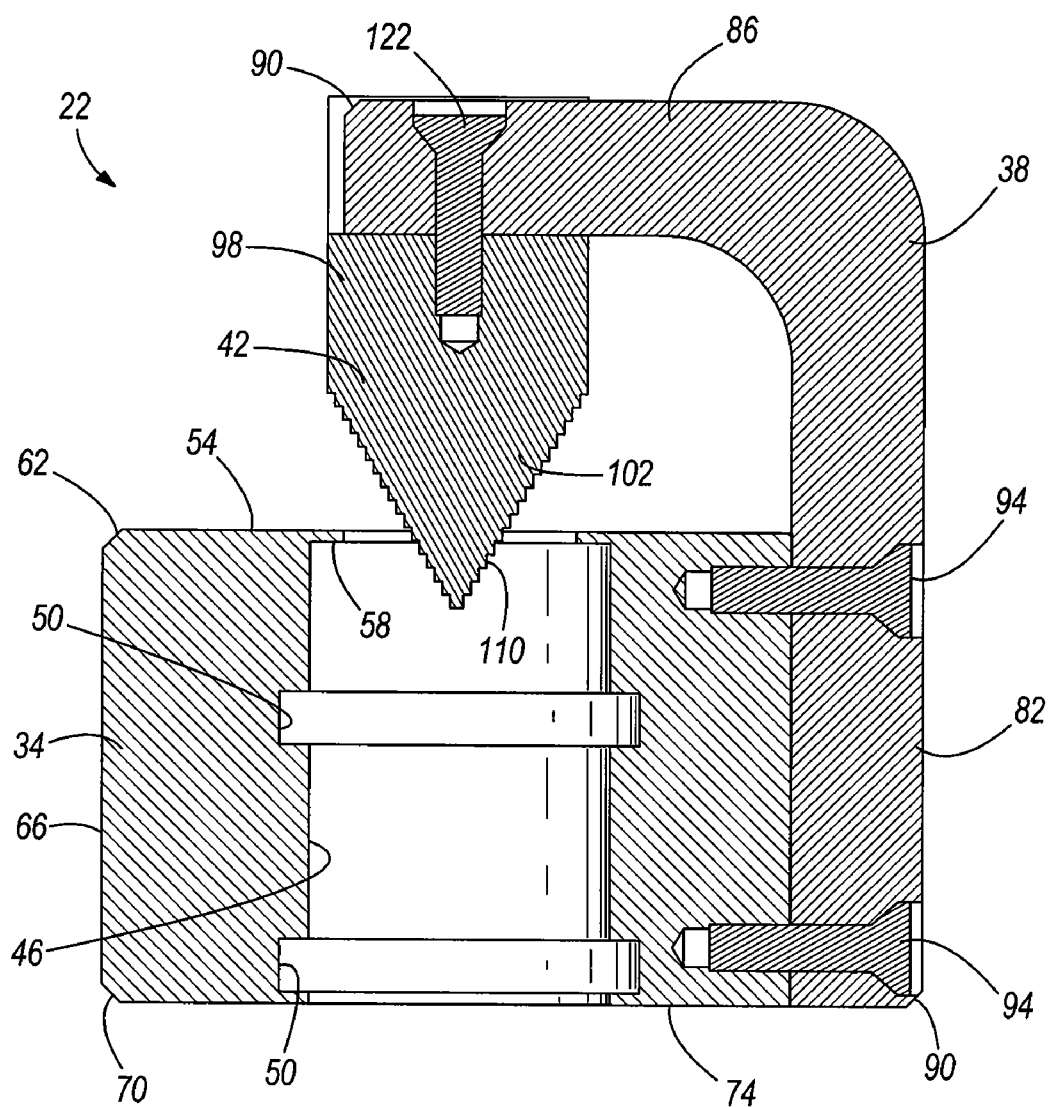
FIG. 3 is a cross-sectional view of the baffle shown in FIG. 1.

As shown in FIGS. 2 and 3, the baffle 22 includes a base 34 and a bullet 42. The base 34 is positioned around a portion of the inlet tube 18 to couple the baffle 22 to the particle counter 10. In the illustrated construction, the base 34 is shown as a separate component coupled to the housing 14. In other constructions, the base 34 may be integrally formed with the inlet tube 18 and/or the housing 14 as a single, unitary structure. The base 34 includes a bore 46 extending therethrough that is sized and configured to correspond to the size and shape of the inlet tube 18.

As shown in FIG. 3, the bore 46 includes a pair of channels 50 circumferentially surrounding the bore 46. Each channel 50 is configured to receive an elastomeric band or O-ring 52 (FIG. 2) to provide a frictional engagement between the base 34 and the inlet tube 18, releasably securing the baffle 22 to the particle counter 10. In some constructions, the base 34 may also or alternatively be coupled to the housing 14 with fasteners (e.g., screws, bolts, nails, pins, etc.).

The base 34 also includes a flange surface 54 positioned opposite from the housing 14. The flange surface 54 extends substantially perpendicularly around the inlet tube 18 at approximately the same height as the top of the inlet tube 18. The inner diameter of the flange surface 54 is slightly smaller than the diameter of the bore 46, forming a lip 58 on which the base 34 contacts and rests on the inlet tube 18. The flange surface 54 improves large particle collection by increasing the lateral velocity of air drawn through the inlet tube 18. In addition, the flange surface 54 limits the air that is drawn into the inlet tube 18 to that which is substantially above the flange surface 54.

As shown in FIG. 3, the base 34 further includes an upper chamfered edge 62 between the flange surface 54 and an outer surface 66 of the base 34 and a lower chamfered edge 70 between a bottom surface 74 and the outer surface 66 to reduce the number of sharp edges on the base 34.

In the illustrated construction, the base 34 further includes an arm 38 having a first portion 82 and a second portion 86 integrally formed into a single component in a generally L-shaped configuration. Similar to above, edges (e.g., edge 90) of the arm 38 are chamfered to reduce the overall sharpness of the arm 38. A recess 78 (FIG. 2) is formed on the outer surface 66 of the base 34 between the edges 62, 70. The recess 78 extends parallel to the bore 46 and is configured to receive the first portion 82 of the arm 38 to facilitate aligning and coupling the arm 38 to the base 34. The first portion 82 is positioned within the recess 78 and is coupled to the base 34 by a pair of fasteners 94. The first portion 82 extends upwardly past the flange surface 54 of the base 34. The second portion 86 extends generally perpendicularly from the first portion 82 such that the second portion 82 is positioned above and spaced apart from the inlet tube 18 and the flange surface 54 of the base 34. The second portion 86 is configured to receive a portion of the bullet 42 to couple and secure the bullet 42 relative to the inlet tube 18. In other constructions, the base 34 may include other elements configured to support the bullet 42 relative to the inlet tube 18. Alternatively, the arm 38 may comprise substantially all of the base 34 and may be coupled to the housing 14 and/or the inlet tube 18 directly to support the bullet 42.

The illustrated bullet 42 includes a generally cylindrical portion 98, a generally conical portion 102, and a slot 106. The cylindrical portion 98 and the conical portion 102 may be coupled together (e.g., by brazing, welding, fasteners, etc.) or may be integrally formed into a single component. The bullet 42 is typically sized to maintain relatively the same overall size of existing particle counters. That is, the bullet 42 is configured such that when the baffle 22 is installed on the particle counter 10, the particle counter 10 takes up substantially the same amount of space as a particle counter without a baffle. Although the bullet 42 is shown and described as being generally circular in cross-section, it should be readily apparent to one skilled in the art that the bullet 42 can have a cross-section corresponding to the shape of the inlet 26. As such, the conical portion 102 may be pyramidal, irregular, or the like depending on the cross-sectional shape of the inlet 26. In addition, the cylindrical portion 98 may likewise be a different shape to correspond with the inlet 26, or may be omitted entirely and yet be considered bullet shaped. It is also envisioned that the shape of the conical portion 102 and/or the cylindrical portion 98 may be different from the shape of the inlet 26, and that the cylindrical portion 98 may have a varying cross-sectional area.

The cylindrical portion 98 can be sized such that a cross-sectional area (or a diameter) of the cylindrical portion 98 perpendicular to the axis 30 is approximately the same size as a cross-sectional area (or a diameter) of the inlet 26 perpendicular to the axis 30. In one construction, the cross-sectional area of the bullet 42 is between about seventy-five percent smaller than the cross-sectional area of the inlet 26 and about three-hundred percent larger than the cross-sectional area of the inlet 26. In a preferred construction, the cross-sectional area of the bullet 42 is between about zero and about forty percent larger than the cross-sectional area of the inlet 26. In an even more preferred construction, the cross-sectional area of the bullet 42 is between about twenty-five and about thirty percent larger than the cross-sectional area of the inlet 26. In a construction where the bullet 42 and the inlet 26 are generally circular, the bullet 42 has a diameter of about 0.50 inches while the inlet 26 has a diameter of about 0.44 inches. In other constructions, different dimensions corresponding to different cross-sectional shapes may also be utilized. In one construction, the length of the cylindrical portion 98 along the axis is about 0.50 inches or larger. In a preferred construction, the length of the cylindrical portion is between about 0.55 inches and about 0.7 inches.

As shown in FIG. 3, the illustrated conical portion 102 tapers from the cylindrical portion 98 and includes a series of steps 110. In one construction, the total interior angle of the taper is between about thirty degrees and about one-hundred-eighty degrees (i.e., between about fifteen degrees and about ninety degrees from axis 30 to a surface of the taper). In a preferred construction, the total interior angle of the taper is between about fifty degrees and about seventy degrees (i.e., between about twenty-five degrees and about thirty-five degrees from axis 30 to a surface of the taper). In an even more preferred construction, the total interior angle of the taper is about sixty degrees (i.e., about thirty degrees from axis 30 to a surface of the taper). In the illustrated construction, the steps 110 are generally right angle steps that each extend around the entire circumference of the conical portion 102. That is, each step 110 includes a surface that is substantially perpendicular to the axis 30 and a surface that is substantially parallel to the axis 30. In one construction, the steps 110 are about 0.024 inches high (i.e., the vertical distance between steps 110) and about 0.014 inches wide (i.e., the radial difference between steps 110). In other constructions, the height and/or width of the steps 110 may be larger or smaller, and the steps 110 may not be uniform or configured as right angles. The generally small size of the steps 110 has a negligible effect on airflow or larger particle entrapment. In addition, the steps 110 prevent steep downward reflection of laterally incoming light (i.e., light coming in off axis, not from directly overhead) and, instead, reflect the light towards the sides of the inlet tube 18, causing more reflections before the light reaches a detector within the housing 14.

Figures 7, 8, 9:
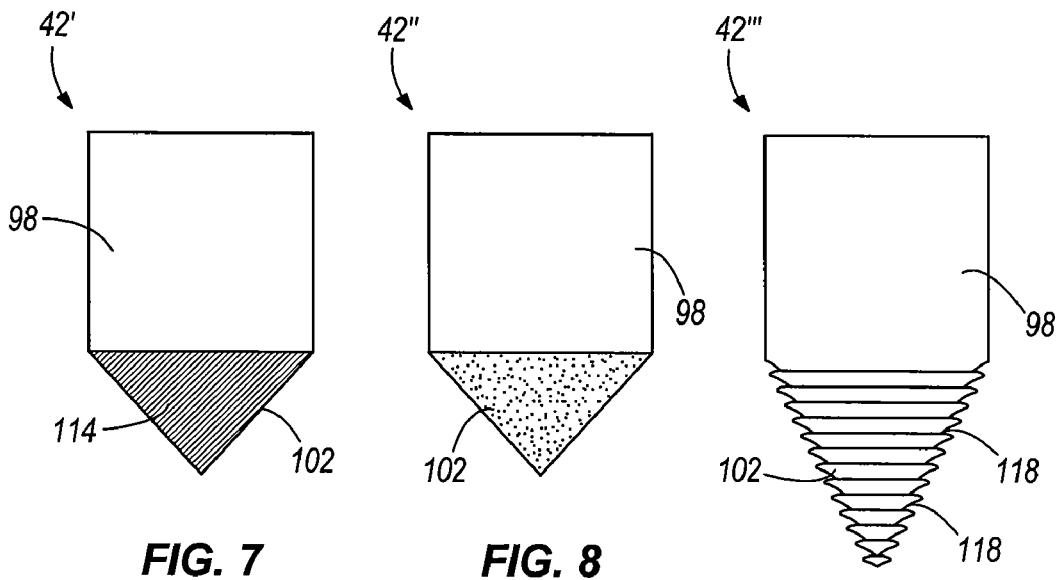
FIGS. 7-9 illustrate additional constructions of a bullet of the baffle.

In other constructions, the conical portion 102 may include other features to limit the amount of light reflected into the inlet tube 18. For example, the conical portion 102 may be coated with a light absorbing paint 114 (FIG. 7), may be roughened by bead blasting (FIG. 8), or may include a series of grooves 118 (FIG. 9). The grooves 118, which may be uniform or non-uniform, are configured such that some or all of the surfaces of each groove 118 are at a substantially non-perpendicular and non-parallel angle with respect to the axis 30. Additionally, the conical portion 102 may include any suitable combination of these, as well as other, features.

Figure 4:
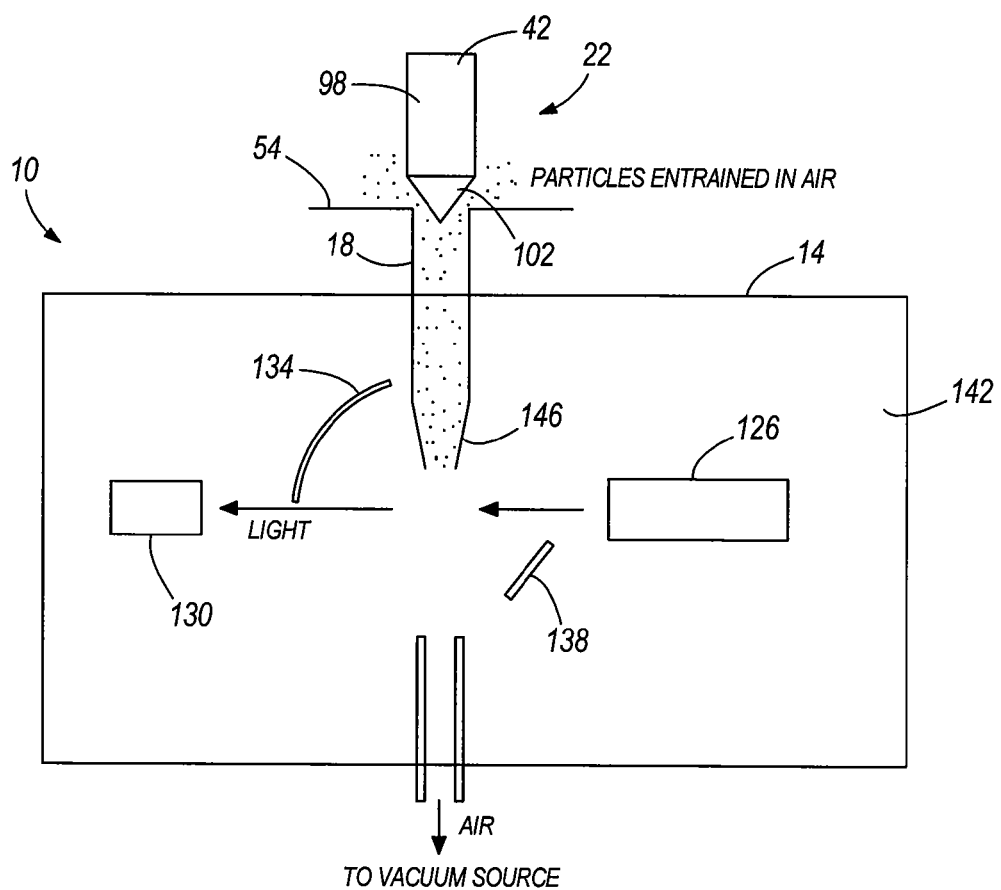
FIG. 4 is a schematic of the particle counter shown in FIG. 1.

The slot 106 receives the second portion 86 of the arm 38 to couple the bullet 42 to the arm 38 with a fastener 122. The bullet 42 is thereby secured such that a portion of the conical portion 102 extends downwardly into the inlet tube 18, as shown in FIGS. 3 and 4. In other constructions, the apex of the conical portion 102 may be generally aligned with the top of the inlet tube 18, or the conical portion 102 may be spaced slightly apart from (e.g., above) the inlet tube 18. In one construction, the placement of the bullet 42 is such that the distance from the closest cross-sectional area of the cylindrical portion 98 to the surface 54 is between about fifty percent and about one-hundred-fifty percent of the radius of the inlet 26. In a preferred construction, the placement of the bullet 42 is such that the distance from the closest cross-sectional area of the cylindrical portion 98 to the surface 54 is between about eighty percent and about one-hundred-twenty percent of the radius of the inlet 26. In an even more preferred construction, the placement of the bullet 42 is such that the distance from the closest cross-sectional area of the cylindrical portion 98 to the surface 54 is about one-hundred percent of the radius of the inlet 26.

As shown in the exemplary construction of FIG. 4, the particle counter 10 includes a light source 126, a receiver 130, at least one mirror or lens 134, a detector 138, and a vacuum source. In operation, the vacuum source (e.g., a pump) draws an airflow past the baffle 22 and through the inlet tube 18 towards a scattering chamber 142. The baffle 22 uses the moving airflow to steer the particles toward the center of the inlet tube 18 (i.e., the axis 30), while at the same time reducing the amount of overhead light entering the inlet tube 18 to an acceptable level and without restricting the airflow. The airflow is slightly constrained by a nozzle 146 at an end of the inlet tube 18 positioned within the scattering chamber 142. Inside the scattering chamber 142, the airflow is illuminated by a beam of light from the light source 126 (e.g., a laser) and particles in the airflow scatter some of the light. The scattered light is directed by the mirror(s) and/or lens(es) 134 in the scattering chamber 142 onto the detector 138 (e.g., a light sensitive detector), producing electrical pulses that may be sized and counted. In situations where particles are not present to scatter the light or some of the light passes through the airflow without contacting a particle, the light is absorbed by the receiver 130 (e.g., a light absorber).

Figure 5:
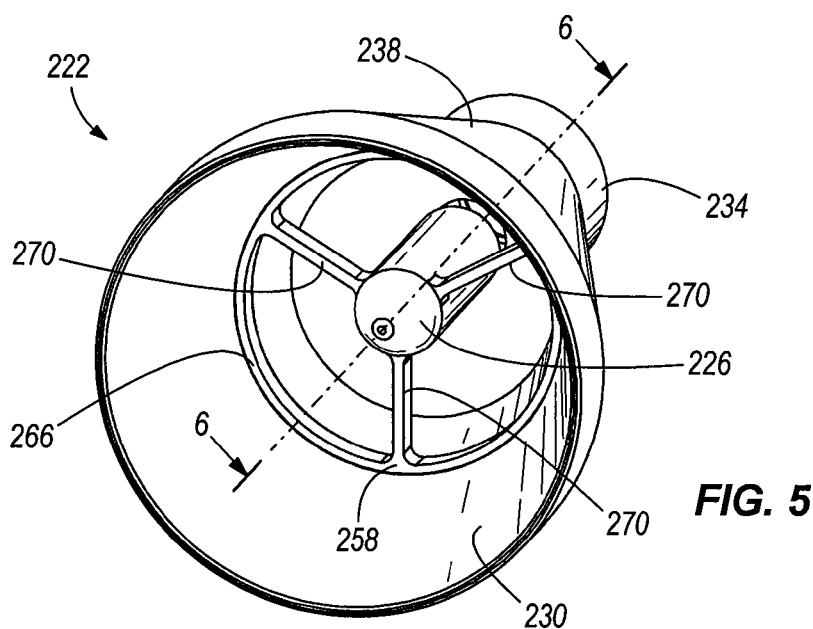
FIG. 5 is a perspective view of an isoprobe for use with the particle counter shown in FIG. 1.
Figure 6:
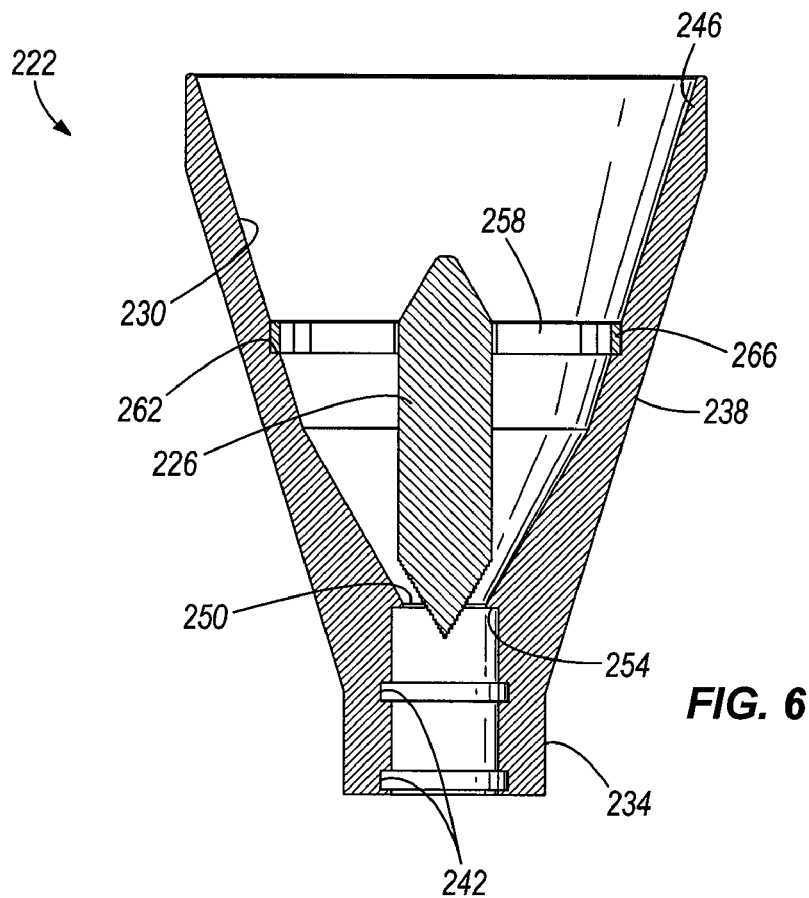
FIG. 6 is a cross-sectional view of the isoprobe shown in FIG. 5 taken through line 6-6.

FIGS. 5 and 6 illustrate another baffle for use with an environmental sensor such as the illustrated particle counter 10. In the illustrated construction, the baffle is configured as an isokinetic probe (i.e., an isoprobe) having a bullet 226 positioned within the isoprobe 222. The isoprobe 222, or base, is generally funnel-shaped and suitable for use in situations where a slight downdraft of air is present. The isoprobe 222 includes a bore 230 having a cylindrical portion 234 configured to receive the inlet tube 18 and a conical portion 238. The cylindrical portion 234 includes a pair of spaced apart channels 242, each configured to receive an elastomeric band or O-ring to frictionally engage the inlet tube 18.

The conical portion 238 includes a larger, open end 246 that tapers toward a smaller end 250 adjacent to the inlet tube 18. The conical portion 238 may taper smoothly, abruptly, or at varying degrees towards the smaller end 250. In the illustrated construction, the smaller end 250 has a cross-sectional area approximately the same as the cross-sectional area of the inlet tube 18, forming a lip 254 on which the isoprobe 222 contacts and rests on the inlet tube 18. The larger end 246 of the isoprobe 222 is sized and configured to receive air from the surrounding environment and direct the air towards the smaller end 250. For example, the larger end 246 is sized such that the downdraft speed of the air times the cross-sectional area of the larger end 246 equals the airflow rate through the particle counter 10.

The bullet 226 is substantially similar to the bullet 42, and alternative bullets 42', 42'', 42''', described above. Reference is hereby made to the above bullets 42, 42', 42'', 42''' for description of the features and elements of the bullet 226 in FIGS. 5 and 6.

In the illustrated construction, the bullet 226 is supported within the isoprobe 222 by a guide 258. The guide 258 is positioned within the isoprobe 222 and engages a ledge 262 on the inside of the conical portion 238. As shown in FIG. 5, the guide 258 includes an annular ring 266 and three spokes 270 extending radially inwardly to engage and support the bullet 226. As such, the bullet 226 may be formed as a single, integral component with the guide 266 or may be a separate component coupled to the spokes 270. For example, the bullet 226 may be brazed, welded, glued, or coupled with fasteners to the spokes 270.

In operation, the funnel shape of the isoprobe 222 facilitates directing larger particles toward the inlet tube 18. With the isoprobe 222, some of the particles that would otherwise miss the inlet tube 18 (e.g., due to the air downdraft or limited mobility of the particles) are also directed toward the inlet tube 18. The particles then travel through the inlet tube 18 to the scattering chamber 142 of, for example, the particle counter 10 and are monitored and counted as described above with reference to FIG. 4.

Various features and advantages of the invention are set forth in the following claims.

What is claimed is:

1. A baffle for use wit a particle counter, the particle counter including a housing supporting an interior chamber, a light source configured to provide illumination to the interior chamber, a light detector configured to detect a light characteristic within the interior chamber, and an inlet configured for the directional passage of airborne particles from outside of the housing to the interior chamber, the inlet having an inlet axis and defining a first cross-sectional area with respect to the inlet axis, the baffle comprising a bullet configured to be positioned adjacent to the inlet of the particle counter and having a bullet axis oriented substantially co-linearly along the inlet axis, the bullet having a second cross-sectional area with respect to the bullet axis that is between about seventy-five percent smaller than the first cross-sectional area and about three-hundred percent larger tan the first cross-sectional area.

2. The baffle of claim 1, further comprising a base coupled to the bullet.

3. The baffle of claim 2, wherein the inlet includes an inlet tube extending from the housing, and wherein the base defines a bore configured to receive at least a portion of the inlet tube.

4. The baffle of claim 2, wherein the base includes an arm coupled to the bullet, and wherein the arm supports the bullet relative to the inlet.

5. The baffle of claim 2, wherein the base includes a surface extending substantially perpendicularly around at least a portion of the inlet.

6. The baffle of claim 2, wherein the base is an isoprobe coupled to the inlet and defining a generally funnel-shaped passageway, and wherein a substantial portion of the bullet is positioned within the generally funnel-shaped passageway of the isoprobe.

7. The baffle of claim 6, further comprising a guide positioned within the isoprobe and coupled to the bullet, and wherein the guide supports the bullet relative to the inlet.

8. The baffle of claim 1, wherein the bullet includes a generally conical portion adjacent to the inlet, the generally conical portion having a surface configured to substantially inhibit light from entering the inlet.

9. The baffle of claim 8, wherein the surface includes at least one step.

10. The baffle of claim 8, wherein the surface includes at least one groove.

11. The baffle of claim 8, wherein at least a portion of the surface is roughened.

12. The baffle of claim 1, wherein the second cross-sectional area is between about zero and about forty percent larger than the first cross-sectional area.

13. The baffle of claim 1, wherein the second cross-sectional area is between about twenty-five and about thirty percent larger than the first cross-sectional area.

14. The baffle of claim 1, wherein a portion of the bullet extends into the inlet.

15. The baffle of claim 1, wherein the first cross-sectional area is generally circular and has a first diameter, and the second cross-sectional area is generally circular and has a second diameter, the second diameter being approximately the same as the first diameter.

16. A particle counter comprising:
a housing;
an interior chamber supported by the housing;
a radiation source to provide radiation to the interior chamber;
a radiation detector configured to detect a characteristic relating to the radiation within the interior chamber;
an inlet configured for the directional passage of airborne particles from outside of the housing to the interior chamber, the inlet having an inlet axis and defining a first cross-sectional area with respect to the inlet axis; and
a baffle including a bullet positioned adjacent to the inlet and having a bullet axis oriented substantially co-linearly along the inlet axis, the bullet having a second cross-sectional area with respect to the bullet axis that is between about seventy-five percent smaller than the first cross-sectional area and about three-hundred percent larger than the first cross-sectional area.

17. The particle counter of claim 16, wherein the baffle further includes a base coupled to the bullet and the housing.

18. The particle counter of claim 17, wherein the inlet includes an inlet tube extending from the housing, and wherein the base defines a bore configured to receive at least a portion of the inlet tube.

19. The particle counter of claim 17, wherein the base includes an arm coupled to the bullet, and wherein the arm supports the bullet relative to the inlet.

20. The particle counter of claim 17, wherein the base includes a surface extending substantially perpendicularly around at least a portion of the inlet.

21. The particle counter of claim 17, wherein the base is an isoprobe coupled to the inlet and defining a generally funnel-shaped passageway, and wherein a substantial portion of the bullet is positioned within the generally funnel-shaped passageway of the isoprobe.

22. The particle counter of claim 21, wherein the baffle includes a guide positioned within the isoprobe and coupled to the bullet, and wherein the guide supports the bullet relative to the inlet.

23. The particle counter of claim 16, wherein the bullet includes a generally conical portion adjacent to the inlet, the generally conical portion having a surface configured to substantially inhibit light from entering the inlet.

24. The particle counter of claim 16, wherein the second cross-sectional area is between about zero and about forty percent larger than the first cross-sectional area.

25. The particle counter of claim 16, wherein a portion of the bullet extends into the inlet.

26. The particle counter of claim 16, wherein the first cross-sectional area is generally circular and has a first diameter, and the second cross-sectional area is generally circular and has a second diameter, the second diameter being approximately the same as the first diameter.

27. An environmental sensor comprising:
a housing;
an interior chamber supported by the housing;
a radiation source configured to irradiate a portion of the interior chamber;
a radiation detector configured to detect a radiation characteristic within the interior chamber;
an inlet configured for the directional passage of a gas from outside of the housing to the interior chamber, the inlet having an inlet axis and defining a first cross-sectional area with respect to the inlet axis; and a baffle including a bullet positioned adjacent to the inlet and having a bullet axis oriented substantially co-linearly along the inlet axis, the bullet having a second cross-sectional area with respect to the bullet axis that is between about seventy-five percent smaller than the first cross-sectional area and about three-hundred percent larger than the first cross-sectional area.

28. The environmental sensor of claim 27, wherein the bullet includes a generally conical portion adjacent to the inlet, the generally conical portion having a surface configured to substantially inhibit light from entering the inlet.

29. The environmental sensor of claim 27, wherein the second cross-sectional area is between about zero and about forty percent larger than the first cross-sectional area.

30. The environmental sensor of claim 27, wherein the baffle further includes a base coupled to the bullet, the base including a surface extending substantially perpendicularly around at least a portion of the inlet.

31. The environmental sensor of claim 30, wherein the inlet includes an inlet tube extending from the housing, and wherein the base defines a bore configured to receive at least a portion of the inlet tube.

* * * * *